United States Patent
Kuyava et al.

(10) Patent No.: US 6,935,847 B2
(45) Date of Patent: Aug. 30, 2005

(54) SPONTANEOUS INFLATION INHIBITOR FOR INFLATABLE PROSTHESIS

(75) Inventors: Charles C. Kuyava, Eden Prairie, MN (US); John W. Westrum, Jr., Prior Lake, MN (US); David W. Clark, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 101 days.

(21) Appl. No.: 10/313,251

(22) Filed: Dec. 6, 2002

(65) Prior Publication Data

US 2003/0065249 A1 Apr. 3, 2003

Related U.S. Application Data

(62) Division of application No. 09/749,256, filed on Dec. 27, 2000, now Pat. No. 6,533,719.

(51) Int. Cl.[7] .......................... F04B 49/00; F16K 39/00; F16K 17/36; A61M 5/00; A61M 9/22
(52) U.S. Cl. .................. 417/278; 417/297; 417/572; 251/282; 604/891.1; 604/8; 604/153; 604/283; 137/78.1; 137/512
(58) Field of Search ................................ 417/278, 297, 417/441, 572; 251/282; 137/512, 78.1; 604/891.1, 892.1, 8, 153, 288.3

(56) References Cited

U.S. PATENT DOCUMENTS

| | | |
|---|---|---|
| 988,120 A | 3/1911 | Lott |
| 1,863,057 A | 6/1932 | Innes |
| 3,312,215 A | 4/1967 | Silber |
| 3,344,791 A | 10/1967 | Foderick |
| 3,397,699 A | 8/1968 | Kohl |
| 3,503,400 A | 3/1970 | Osthagen et al. |
| 3,642,004 A | 2/1972 | Osthagen et al. |
| 3,731,670 A | 5/1973 | Loe |
| 3,797,478 A | 3/1974 | Walsh et al. |
| 3,812,841 A | 5/1974 | Issacson |
| 3,873,063 A * | 3/1975 | Illing .......................... 251/282 |
| 3,954,102 A | 5/1976 | Buuck |
| 4,222,377 A | 9/1980 | Burton |
| 4,267,829 A | 5/1981 | Burton et al. |
| 4,344,434 A | 8/1982 | Robertson |
| 4,383,525 A | 5/1983 | Scott et al. |
| 4,407,278 A | 10/1983 | Burton et al. |
| 4,412,530 A | 11/1983 | Burton |
| 4,441,491 A * | 4/1984 | Evans, Sr. .................... 600/40 |
| 4,453,536 A | 6/1984 | Abild |
| 4,489,732 A | 12/1984 | Hasson |
| 4,537,183 A | 8/1985 | Fogarty |
| 4,553,959 A | 11/1985 | Hickey et al. |
| 4,566,446 A | 1/1986 | Fogarty |
| 4,571,241 A | 2/1986 | Christopher |
| 4,590,927 A * | 5/1986 | Porter et al. .................. 600/40 |
| 4,632,435 A | 12/1986 | Polyak |
| 4,671,261 A | 6/1987 | Fischell |
| 4,682,583 A | 7/1987 | Burton et al. |
| 4,697,619 A * | 10/1987 | Tiefenthaler ................ 137/613 |
| 4,710,169 A | 12/1987 | Christopher |

(Continued)

FOREIGN PATENT DOCUMENTS

DE        2537506        3/1977

*Primary Examiner*—Cheryl Tyler
*Assistant Examiner*—Timothy P. Solak
(74) *Attorney, Agent, or Firm*—Kagan Binder, PLLC

(57) ABSTRACT

A pump assembly for a penile implant is provided having a mechanism which prevents spontaneous inflation of the cylinders implanted within the user. The preventative mechanism uses overpressure generated by the reservoir during unintentional compression to effectively seal the pump assembly from unintended fluid flow. The prevention mechanism itself creates all necessary forces to prevent the undesired fluid flow to the cylinders. This is accomplished by incorporating appropriate mechanisms within the pump itself.

33 Claims, 12 Drawing Sheets

U.S. PATENT DOCUMENTS

| | | |
|---|---|---|
| 4,718,410 A | 1/1988 | Hakky |
| 4,782,826 A | 11/1988 | Fogarty |
| 4,850,963 A | 7/1989 | Sparks et al. |
| 4,932,938 A | 6/1990 | Goldberg et al. |
| 4,944,732 A | 7/1990 | Russo |
| 4,958,630 A | 9/1990 | Rosenbluth et al. |
| 4,968,294 A | 11/1990 | Salama |
| 5,030,199 A | 7/1991 | Barwick et al. |
| 5,034,009 A | 7/1991 | Mouchel |
| 5,041,092 A | 8/1991 | Barwick |
| 5,048,510 A | 9/1991 | Hauschild et al. |
| 5,048,511 A | 9/1991 | Rosenbluth et al. |
| 5,062,417 A | 11/1991 | Cowen |
| 5,063,914 A | 11/1991 | Cowen |
| 5,074,849 A | 12/1991 | Sachse |
| 5,085,650 A | 2/1992 | Giglio |
| 5,088,980 A | 2/1992 | Leighton |
| 5,090,424 A | 2/1992 | Simon et al. |
| 5,112,295 A | 5/1992 | Zinner et al. |
| 5,114,398 A | 5/1992 | Trick et al. |
| 5,131,906 A | 7/1992 | Chen |
| 5,141,509 A * | 8/1992 | Burton et al. .................. 600/40 |
| 5,167,611 A | 12/1992 | Cowan |
| 5,171,272 A | 12/1992 | Levius |
| 5,186,180 A | 2/1993 | Bellas |
| 5,250,020 A | 10/1993 | Bley |
| 5,344,388 A | 9/1994 | Maxwell et al. |
| 5,704,895 A | 1/1998 | Scott et al. |
| 5,851,176 A * | 12/1998 | Willard ....................... 600/40 |
| 5,895,424 A | 4/1999 | Steele, Sr. et al. |
| 6,171,233 B1 | 1/2001 | Willard |
| 6,533,719 B2 | 3/2003 | Kuyava et al. |

* cited by examiner

SPONTANEOUS INFLATION INHIBITOR FOR INFLATABLE PROSTHESIS

CROSS REFERENCE TO RELATED APPLICATIONS

This application is a divisional of U.S. patent application Ser. No. 09/749,256, filed Dec. 27, 2000, now U.S. Pat. No. 6,533,719.

BACKGROUND OF THE INVENTION

This invention generally relates to a pump for inflating a prostheses and more particularly to a pump and valve assembly including a diaphragm which inhibits spontaneous inflation of the prosthesis.

One common treatment for male erectile dysfunction is the implantation of a penile prosthesis. Such a prosthesis typically includes a pair of inflatable cylinders which are fluidly connected to a fluid reservoir via a pump and valve assembly. The two cylinders are normally implanted into the corpus cavernosae of the user and the reservoir is typically implanted in the user's abdomen. The pump assembly is implanted in the scrotum. During use, the user actuates the pump and fluid (typically liquid) is transferred from the reservoir through the pump and into the cylinders. This results in the inflation of the cylinders and thereby produces the desired penis rigidity for a normal erection. Then, when the user desires to deflate the cylinders, a valve assembly within the pump is actuated in a manner such that the fluid in the cylinders is released back into the reservoir. This deflation then returns the penis to a flaccid state.

With inflatable penile prostheses of current designs, spontaneous inflation of the cylinders is known to occasionally occur due to inadvertent compression of the reservoir. Specifically, this inadvertent compression results in the undesired introduction of fluid into the cylinders. While this does not create a medical or physical problem, such inadvertent inflation can be uncomfortable and embarrassing for the user. This undesirable condition is further described below with reference to a particular prosthetic design.

With reference to FIG. 1, a known pump and valve assembly 8 for use in a penile prosthesis includes a fluid input 10 that is coupled at one end to a reservoir (not shown) and to a housing 12 at its opposite end. Also connected to the housing 12 is a fluid output 14 which, in turn, is connected at its other end to a pair of cylinders (not shown). Linking the fluid input 10 and the fluid output 14 to each other is a common passageway 33, which itself contains a valve assembly that is described in greater detail below. Common passageway 33 is also in fluid communication with a pump bulb 18 that is used to move fluid from the reservoir (not shown) to the cylinders (not shown) in order to inflate the cylinders. The valve assembly located within common passageway 33 includes a reservoir poppet 20 which is biased against a valve seat 24 by a spring 28 and a cylinder poppet 22 which is biased against a valve seat 26 by a spring 30. The springs 28 and 30 are sized so as to keep the reservoir poppet 20 and the cylinder poppet 22 biased against each respective valve seat 24 and 26 under the loads that are encountered when the reservoir is pressurized to typical abdominal pressures.

When the user wishes to inflate the cylinders, pump bulb 18 is squeezed so as to force fluid from the pump bulb 18 into the common passageway 33. The resulting fluid flow creates a fluid pressure on reservoir poppet 20 which compliments the force of the spring 28 to hold the reservoir poppet 20 against valve seal 24. The fluid flow also causes compression of the spring 30, and thereby opening cylinder poppet 22. As a result, the fluid travels out through fluid output 14 and into the respective cylinders.

When the user releases the pump bulb 18 a vacuum is created, thus pulling the poppet 22 back against valve seat 26 (aided by spring 30) and simultaneously pulling the reservoir poppet 20 away from its valve seat 24, against the spring 28. As a result, fluid from the reservoir is thus allowed to flow through the fluid input 10 to the common passageway 33, passing around the reservoir poppet 20. Fluid then will freely flow into the vacuous pump bulb 18. Once the pump bulb 18 has been filled, the negative pressure is eliminated and the reservoir poppet 20 returns to its normal position. This pumping action of the pump bulb 18 and valve assembly is repeated until the cylinders are fully inflated as desired.

To deflate the cylinders, the user grips the housing 12 and compresses it along the axis of reservoir poppet 20 and cylinder poppet 22 in a manner such that the wall 13 of the housing 12 contacts the protruding end 21 of the reservoir poppet 20 and forces the reservoir poppet 20 away from valve seat 24. This movement, in turn, causes the reservoir poppet 20 to contact cylinder poppet 22 and force cylinder poppet 22 away from valve seat 26. As a result, both poppets 20 and 22 are moved away from their valve seats 21 and 26 and fluid moves out of the cylinders, through the fluid output 14, through common passageway 33, through the fluid input 10 and back into the reservoir.

Although the springs 28 and 30 are sized to provide sufficient tension to keep poppets 20 and 22 firmly abutted against valve seats 24 and 26 under normal reservoir pressures, it is possible for fluid pressure to exceed the force provided by the springs during heightened physical activity or movement by the user. Specifically, this activity or movement can apply excess pressure to the reservoir. Such excessive pressure on the reservoir may overcome the resistance of the spring-biased poppets 20 and 22 and thereby cause a spontaneous inflation of the cylinders. Encapsulation or calcification of the reservoir can sometimes occur in a patient. This encapsulation could lead to a more snugly enclosed reservoir, thus increasing the possibility of providing excess pressure on the reservoir and the likelihood of spontaneous inflation.

As such, there exists a need to provide a prosthetic penile implant having a spontaneous inflation prevention mechanism that is reliable and easy to operate.

BRIEF SUMMARY OF THE INVENTION

The present invention includes a penile pump having a dual poppet arrangement wherein the poppets act as check valves or flow valves. Each poppet is spring-biased against a valve seat, and under normal circumstances, only allows positive fluid flow when a pump bulb is engaged. To prevent spontaneous inflation when an overpressurization occurs in the reservoir, the same reservoir pressure is utilized to seal the fluid output against itself or to seal one or both of the poppets against the valve seat. Thus, the fluid is prevented from reaching the cylinders and creating a spontaneous inflation. When the movement or activity generating the overpressure in the reservoir is released, the system will return to an equilibrium and allow normal operation. Even if overpressurization of the reservoir is occurring, the pressure generated by compressing the pump bulb will far exceed the level of overpressure. Thus, the poppets will open in the normal way, allowing fluid to flow to the cylinders.

The use of the overpressure in the reservoir itself to prevent fluid flow to the cylinders can be accomplished in a variety of formats. Each of these formats however, generally utilize a structure in fluid communication with the reservoir which is capable of restricting flow caused by reservoir overpressurization.

In a first embodiment, a bypass passageway is provided from the fluid input which terminates in an expansion chamber located directly behind the cylinder poppet. A portion of the housing forms a wall between this chamber and the cylinder poppet. This wall is larger in surface area than the surface area of the cylinder poppet exposed to the overpressure. Since the surface area of the wall is larger than the area of the poppet that contacts the valve seat, the same amount of pressure generated by the reservoir will cause a larger force to be applied by the chamber wall against the poppet than is applied against the poppet through the common passageway. Thus, the cylinder poppet is effectively sealed when an overpressurization occurs in the reservoir.

In another embodiment, the bypass passageway is similarly coupled to the fluid input, bypassing the poppets and terminating in an expansion chamber. The cylinder poppet passageway output leads into a termination chamber connected to the expansion chamber. The expansion chamber is larger than the cylinder poppet output. Located within the expansion chamber is a flexible diaphragm dividing the chamber into two portions. As overpressurization occurs in the reservoir, this pressure is directed through the bypass passageway and is applied to the diaphragm. This pressure causes the diaphragm to flex against the output of the poppet chamber, effectively sealing it. In this sealing position, the diaphragm prevents fluid from reaching the cylinders.

In yet another embodiment, a fluid bypass passageway is provided which connects the fluid input and a chamber which surrounds a portion of compressible tubing. The compressible tubing forms part of the output that leads from the cylinder poppet to the cylinders. As overpressurization occurs in the reservoir, this force is directed along the bypass passageway causing the flexible tubing to compress, thus effectively sealing it off. Once again this prevents fluid flow to the cylinders because the flexible tubing is part of the output.

In a further embodiment, a fluid bypass passageway is provided between the reservoir and a fluid return passageway. The fluid return passageway couples an expansion chamber to an intermediate chamber between the reservoir poppet and the cylinder poppet. A bypass check valve is included in the bypass fluid passageway and allows pressurized fluid to flow from the input chamber into the return passageway. A return check valve is provided within the return fluid passageway between the intermediate chamber and the point where the bypass fluid passageway intersects the return fluid passageway.

Thus, in an overpressure situation, pressurized fluid is allow to flow from the input chamber through the bypass fluid passageway and into the expansion chamber. The expansion chamber includes a flexible abutting wall which is caused to engage the cylinder poppet and to firmly seat it. In this situation, spontaneous inflation is avoided.

While spontaneous inflation is prevented, pressurized fluid is able to enter the intermediate chamber. When the pressure of the fluid in the reservoir and the input chamber is reduced, this pressurized fluid remains in the intermediate chamber. If the expansion chamber were just allowed to relax when fluid pressure in the reservoir is reduced, it may be possible for the pressurized fluid in the intermediate chamber to open the cylinder poppet and partially inflate the cylinders. Thus, by providing this configuration of a bypass fluid passageway and a return passageway with the appropriate check valves, the pressured fluid entering the expansion chamber will be caused to remain there until the fluid pressure in the intermediate chamber is reduced. When the pump bulb is actuated, sufficient pressure is generated to overcome the opposing force generated in the expansion chamber and the cylinder poppet is unseated.

In still another embodiment, a bypass fluid passageway and a return fluid passageway are provided wherein each includes a check valve as previously described. However, in this embodiment, both the bypass fluid passageway and the return fluid passageway are fluidly coupled to the input chamber. In addition, the return fluid passageway is coupled to the intermediate chamber. Located within the return fluid passageway between the intermediate chamber and the input chamber is a fluid resistor.

When an overpressurization situation occurs, pressurized fluid will enter both the expansion chamber and the intermediate chamber. As previously described, the expansion chamber will seat the cylinder poppet firmly against the opening. As fluid pressure is reduced in the reservoir and input chamber, the fluid resistor allows pressurized fluid from the intermediate chamber to bleed back to the input chamber. Thus, eventually, the fluid pressure within the immediate chamber will be lower than the fluid pressure within the expansion chamber. Once this occurs, the return check valve will open and the pressurized fluid within the expansion chamber can return to the input chamber. Due to the configuration of the return check valve and the fluid resistor, pressure levels within the expansion chamber will always be higher than pressure levels within the intermediate chamber and, as a result, the cylinder poppet will always be firmly seated.

In still yet another embodiment, a bypass fluid passageway and a return fluid passageway are provided wherein each is fluidly coupled to the input chamber. A check valve is placed within the bypass fluid passageway which only allows fluid to flow from the input chamber to the expansion chamber. Located within the return channel fluid passageway are a pair of fluid resistors placed on either side of a passageway into the intermediate chamber. When an overpressurization situation occurs, pressurized fluid opens the bypass check valve and allows fluid flow through the bypass fluid passageway to the expansion chamber. This pressurized fluid then firmly seats the cylinder poppet. Pressurized fluid will also enter the intermediate chamber. When pressure is reduced in the reservoir and the input chamber the pressurized fluid trapped within the intermediate chamber is slowly able to bleed through a single fluid resistor into the input chamber. As fluid pressure is reduced in the intermediate chamber and the portion of the return fluid passageway located between the fluid resistors, the pressurized fluid within the expansion chamber is slowly able to bleed through the second fluid resistor and eventually into the input chamber.

In still another embodiment a bypass fluid passageway is provided that couples the input chamber to an expansion chamber. The intermediate chamber is also fluidly coupled to the bypass fluid passageway. A first fluid resistor having a relatively low fluid resistance is placed between the intermediate chamber and the bypass fluid passageway. A second fluid resistor having a higher impedance is placed between the expansion chamber and the intermediate chamber. A bypass channel is constructed around the second fluid resistor and includes a bypass check valve allowing fluid to flow from the bypass fluid passageway around the second fluid resistor and into the expansion chamber. When an over-pressurization situation occurs, pressurized fluid will be trapped within the expansion chamber and the intermediate chamber. When pressure is reduced, pressurized fluid is able to flow from the intermediate chamber through the low impedance fluid resistor through the bypass fluid passageway and info the input chamber. As pressure levels drop within the bypass fluid passageway pressurized fluid will eventually be able to flow from the expansion chamber through the high impedance fluid resistor and into the input chamber. This configuration also ensures that fluid pressure levels within the expansion chamber will always be higher than those within the intermediate chamber (except during actuation of the pump bulb). Thus, preventing spontaneous inflation.

In another embodiment, an input chamber is provided that is connected to the fluid input, prior to the point the fluid input engages the first poppet. At the output of the pump, a passageway leading from the cylinder poppet to the cylinders is caused to narrow in a throat region, which is located proximate the input chamber. When an overpressurization of the reservoir occurs this input chamber is caused to expand, thus forcing its outer walls to move outward. Outward movement of the outer walls effectively seals the throat portion, thus preventing fluid flow from the reservoir from reaching the cylinders.

In still yet another embodiment a separate problem is addressed. Namely inadvertent compression of the valve walls may lead to an unseating of the reservoir and/or cylinder poppet and possibly lead to spontaneous inflation. To prevent this it may be desirable to make the housing substantially more rigid. This can be accomplished by encasing the reservoir and cylinder poppets within a solid cylindrical membrane.

In most of the above outlined embodiments, the force generated by an overpressurization of the reservoir is used to prevent fluid flow into the cylinders.

DETAILED DESCRIPTION OF THE INVENTION

Figure 1:
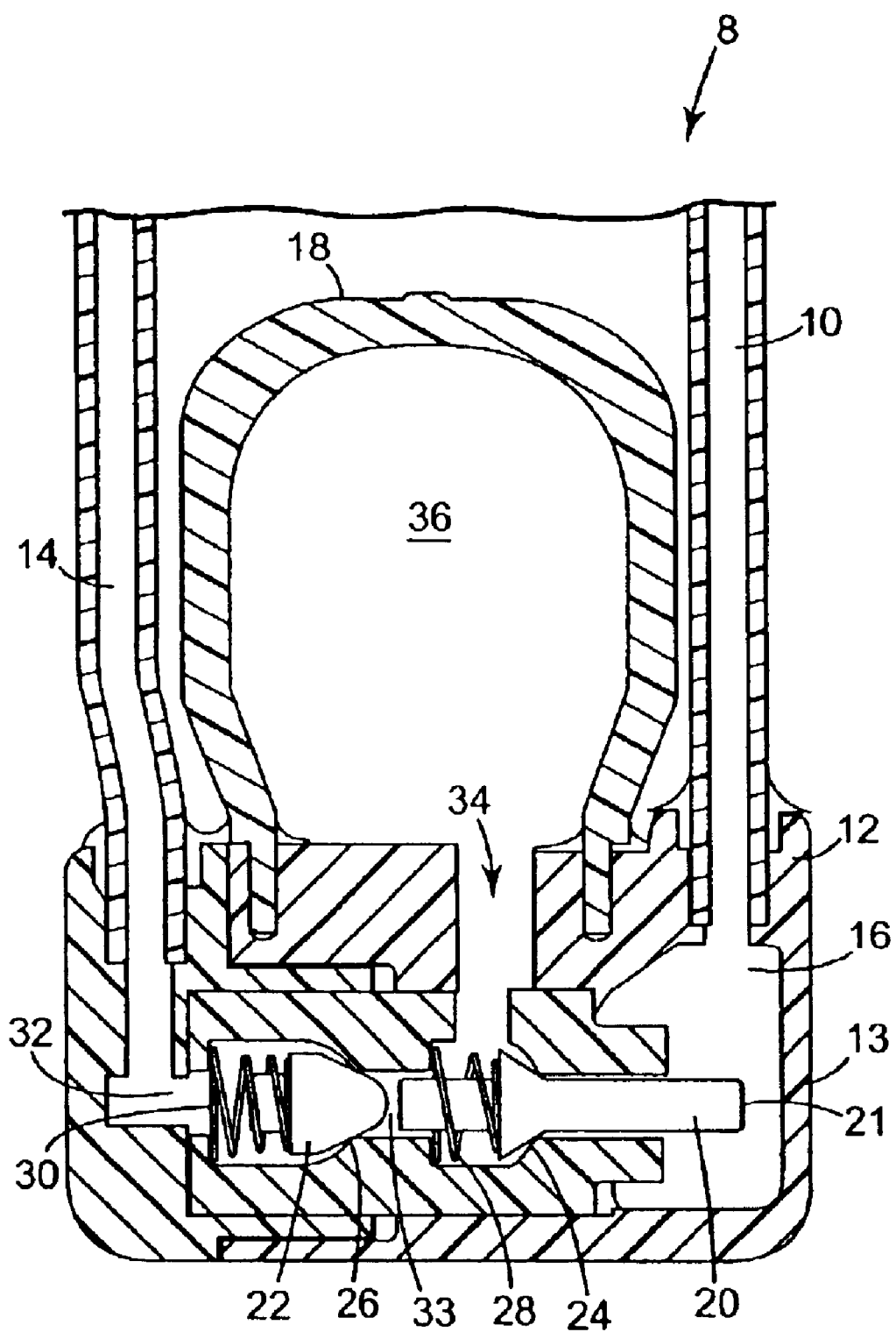
FIG. 1 is a side-sectional view of a penile pump according to the teachings of the prior art.

Referring to FIG. 1, a pump assembly is shown and generally referred to as 8. Pump assembly 8, as illustrated in FIG. 1, is essentially that of the prior art, but an understanding of the working elements of pump assembly 8, as illustrated in FIG. 1, is beneficial to understanding the operation of each embodiment of the present invention. Generally, the pump assembly 8 will be implanted into the user's scrotum. A separate fluid-filled reservoir (not shown) is implanted in some other portion of the user's body, usually in the abdomen. Fluidly connecting the reservoir to the pump assembly 8 is fluid input 10 which will usually be a flexible silicone tube. A pair of inflatable cylinders (not shown) are usually implanted in the user's corpus cavernosae and are fluidly connected to pump assembly 8 via fluid output 14, which is also usually a flexible silicone tube.

In general, when pump assembly 8 is actuated, fluid is drawn from the reservoir through the pump assembly 8 and pumped into the cylinders. During the inflation process and until released by the user, the pump assembly 8 maintains the fluid pressure in the cylinders, thus keeping them in their inflated state. When deflation is desired, the user manipulates assembly 8, permitting fluid to transfer out of the inflatable cylinders and into the reservoir, thereby deflating the cylinders and returning them to a flaccid state.

Pump assembly 8 generally includes a housing 12 usually formed of silicone. Attached to housing 12 is a pump bulb 18, which includes a relatively large pump chamber 36. Fluid input 10 is coupled to the housing 12 and empties into an input chamber 16. As such, fluid input 10 couples input chamber 16 to the reservoir. A common passageway 33 is fluidly coupled between input chamber 16 at one end of the housing 12, and fluid output 14 at an opposite end of the housing 12. Similarly, the pump chamber 36 is fluidly coupled to the common passageway 33 via pump passageway 34.

Disposed within common passageway 33 is a reservoir poppet 20 which functions as a check valve. Reservoir poppet 20 is an elongated member having a contoured portion which abuts reservoir poppet valve seat 24 forming a fluid tight seal. A reservoir poppet spring 28 engages reservoir poppet 20 and biases reservoir poppet 20 against the reservoir poppet valve seat 24. Also disposed within common passageway 33 and in line with reservoir poppet 20 is cylinder poppet 22. Cylinder poppet 22 forms a second check valve within common passageway 33. Cylinder poppet 22 is biased by cylinder poppet spring 30 against cylinder poppet valve seat 26 in a normal state, thereby forming another fluid tight seal within common passageway 33. Reservoir poppet 20 is substantially longer than cylinder poppet 22. A front end of reservoir poppet 20 extends into input chamber 16, in close proximity to an outer wall of housing 12. Furthermore, the front end of cylinder poppet 22 is in close proximity to the rear end of reservoir poppet 20. As such, the user can manipulate both poppets 20 and 22 by compressing the wall of housing 12. Compression of the housing 12 will cause the reservoir poppet 20 to compress reservoir poppet spring 28 thus displacing the reservoir poppet 20 from reservoir poppet valve seat 24. This motion will also cause cylinder poppet 22 to be displaced from cylinder poppet valve seat 26 while compressing cylinder poppet spring 30. When both reservoir poppet 20 and cylinder poppet 22 are displaced from their respective valve seats, fluid is allowed to freely flow between input chamber 16 and fluid output 14, and hence fluid is allowed to freely flow between the reservoir and the cylinders.

During a majority of the time, pump assembly 8 will be in the configuration shown in FIG. 1. That is, both reservoir poppet 20 and cylinder poppet 22 are abutting their respective valve seats 24 and 26, forming a fluid tight seal. When inflation is desired, pump bulb 18 is manually compressed by the user. This forces the fluid in pump chamber 36 out through pump passageway 34 and into common passageway 33, under relatively high pressure. Because of the location of pump passageway 34 with respect to the reservoir poppet 20, this increased pressure causes reservoir poppet 20 to further abut reservoir poppet valve seat 24. This increased pressure is more than sufficient to remove cylinder poppet 22 from its abutment with cylinder poppet valve seat 26, by compressing cylinder poppet spring 30. As such, the pressurized fluid is allowed to pass through a portion of the common passageway 33 and into fluid output 14, where it eventually reaches an inflatable cylinder. When released, the pump bulb 18 expands back to its original configuration, creating negative pressure within pump chamber 36 and common passageway 33. This negative pressure draws cylinder poppet 22 towards valve seat 26 and simultaneously pulls reservoir poppet 20 away from valve seat 24. As such, fluid is drawn from the reservoir, and into pump chamber 36 until the negative pressure is eliminated. Then, reservoir poppet spring 28 causes the reservoir poppet 20 to reseat itself against valve seat 24.

Repeated compression of pump bulb 18 eventually inflates the cylinders to a sufficient degree of rigidity for the user. Once inflated, the fluid remaining in fluid output 14 is under a relatively high degree of pressure. This high pressure fluid aids cylinder poppet spring 30 in forcing cylinder poppet 22 against cylinder poppet valve seat 26 again forming a fluid tight seal and preventing fluid from within the cylinders from passing back through the pump assembly 8 (preventing deflation of the cylinders).

When the user desires deflation of the cylinders, the wall of housing 13 is manually compressed. This compression forces reservoir poppet 20 away from reservoir poppet valve seat 24 and simultaneously causes cylinder poppet 22 to be removed from cylinder poppet valve seat 26. The pressurized fluid within the cylinders and fluid output 14 naturally returns to the reservoir via common passageway 33. Furthermore, the cylinders can be manually compressed forcing out any remaining fluid. Once the cylinders are satisfactorily emptied, the user releases the grip on housing 12, thus allowing cylinder poppet 22 and reservoir poppet 20 to once again abut their respective valve seats 24 and 26.

As described above, pump assembly 8 (as shown in FIG. 1) works relatively well under normal circumstances. However, when the user compresses the reservoir inadvertently through bodily movement, the pressure generated may be sufficient to remove reservoir poppet 20 and cylinder poppet 22 from their respective valve seats 24 and 26, thus spontaneously inflating the cylinders. When sufficient force is generated against the reservoir (or a similar component) to cause the fluid pressure to exceed the resistive characteristics of poppets 20 or 22 (overcome the force of reservoir poppet spring 28 and cylinder poppet spring 30), an overpressure situation has occurred. Of course, the only way to release this spontaneous inflation is to manually release the check valves.

In order to avoid spontaneous inflation, the present invention utilizes the overpressure created by compression of the reservoir to seal off the pump assembly output 14. This solution can be accomplished by many different approaches, a number of which are outlined below. It should be noted that the order in which these different embodiments are presented should not be interpreted to imply any significance or importance to any one embodiment over another.

Figure 2:
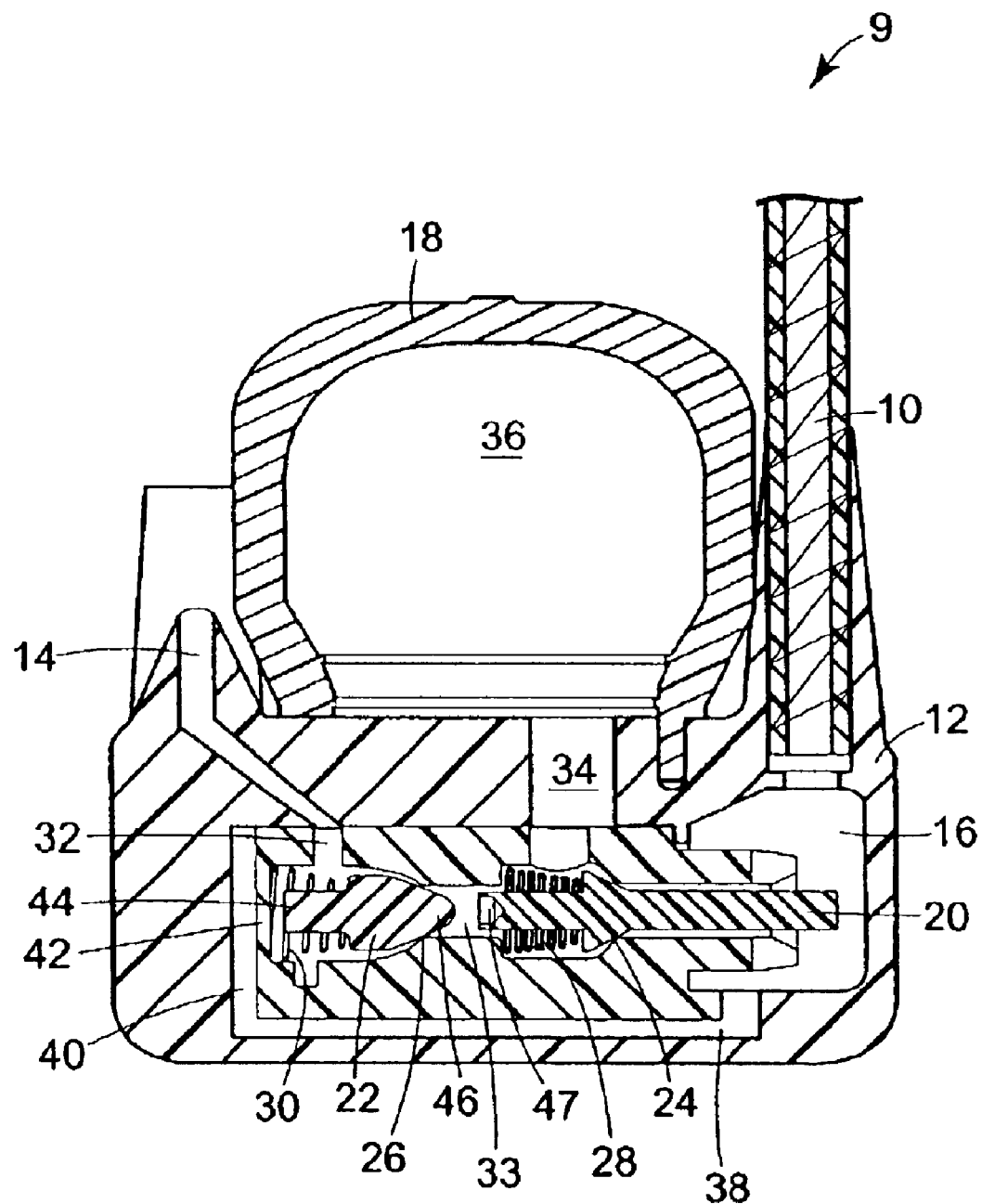
FIG. 2 is a side-sectional view of a penile pump in a state of equilibrium, having a termination chamber which can force the cylinder poppet against a valve seat during an overpressurization situation.

Referring to FIG. 2, a first embodiment of the present invention is shown and described. In summary, an overpressure tolerant pump assembly 9 is provided and including a bypass passageway 38 is added to the system which couples input chamber 16 to an expansion chamber 40. The expansion chamber 40 is provided adjacent to the rear end 44 of cylinder poppet 22. The relatively thin portion of housing 12 that exists between common passageway 33 and expansion chamber 40 forms an abutting wall 42. Abutting wall 42 is relatively flexible and operates very similarly to a flexible diaphragm. Importantly, the planar surface area of abutting wall 42 is greater than the area of nose 46 of cylinder poppet 22 (wherein the nose 46 is that portion of cylinder poppet 22 that would be exposed to overpressure generated by the reservoir when the cylinder poppet 22 is seated against the valve seat 26). This "nose" area is approximately equal to the cross sectional area of the common passageway 33, at a point between the nose 46 and the rear end portion 47 of reservoir poppet 20.

As is shown, expansion chamber 40 forms a closed chamber which has no output. Cylinder poppet output 32 is separate from expansion chamber 40 and couples the common passageway 33 to fluid output 14.

Under normal operation, reservoir poppet 20 and cylinder poppet 22 will function in exactly the same manner as described above with reference to FIG. 1. When an overpressure situation occurs within the reservoir pump assembly, the present invention will appropriately deal with these pressures to avoid spontaneous inflation. When the reservoir is somehow compressed by the user, pressurized fluid is directed through fluid input 10 and into input chamber 16 (pressure is simply increased when fluid is already present). The pressurized fluid will likewise flow into (or increase pressure within) bypass passageway 38 and fill expansion chamber 40. As pressure from the reservoir is increased, expansion chamber 40 is forced to expand, causing abutting wall 42 to press against rear end 44 of cylinder poppet 22, thus achieving the configuration shown in FIG. 3.

Figure 3:
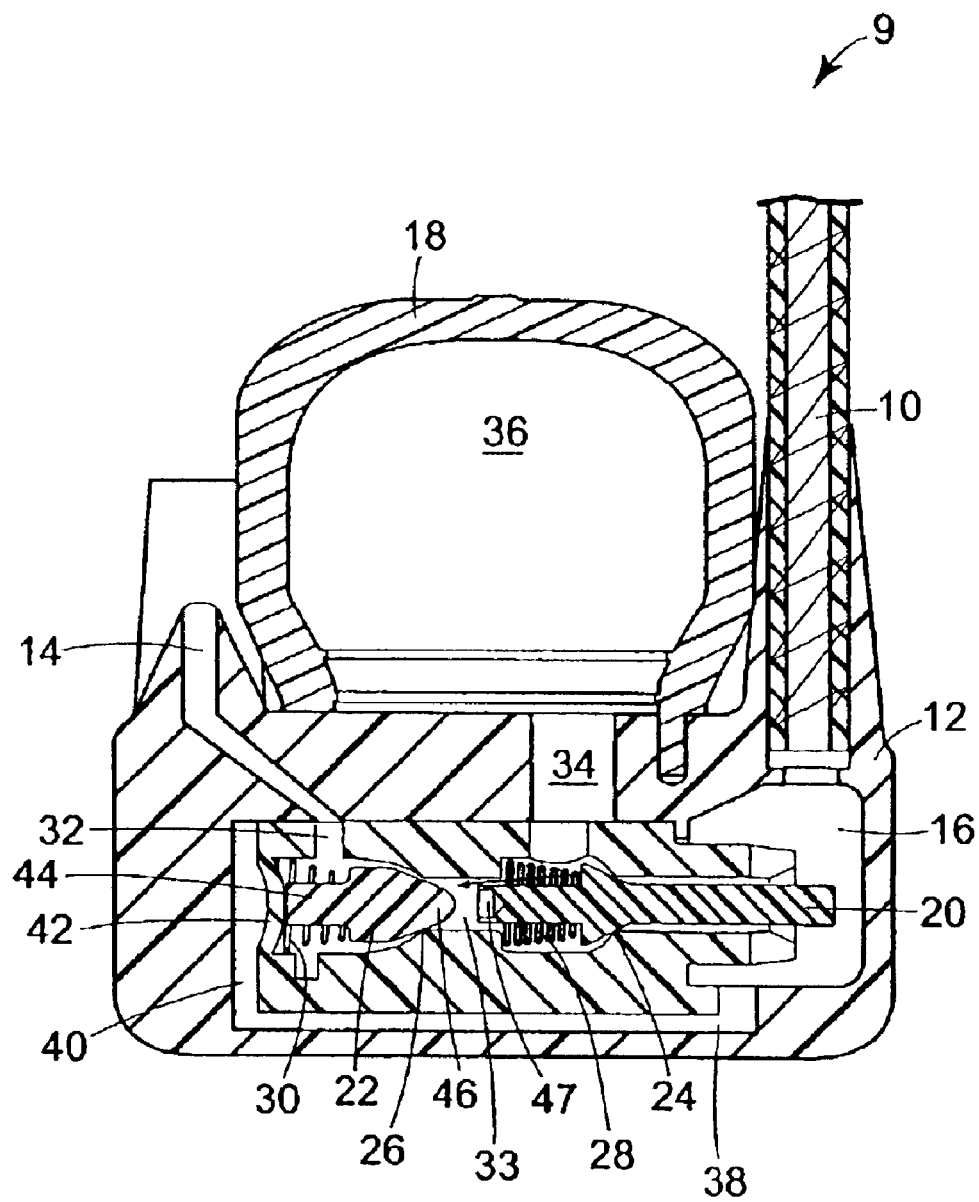
FIG. 3 is a side-sectional view of the penile pump shown in FIG. 2 during an overpressurization situation.

Referring now to FIG. 3, abutting wall 42 forces cylinder poppet 22 against valve seat 26 preventing any fluid from entering the fluid output 14 and inflating the cylinders. Even as the overpressure generated by the reservoir is sufficient to remove reservoir poppet 20 from its valve seat 24, it will typically not be sufficient to remove cylinder poppet 22 from its valve seat 26 because the surface area of the abutting wall 42 (on the expansion chamber 40 side) is larger than the surface area of the nose 46 of cylinder poppet 22. With equal fluid pressure being generated against both the cylinder poppet 22 and the abutting wall 42, more force will be generated by the abutting wall 42 since it has a larger exposed surface area. As such, the overpressure is used against itself to prevent the cylinder poppet 22 from opening and spontaneously inflating the cylinders.

The movement of the expansion chamber 40 causing the abutting wall 42 to engage the cylinder poppet 22 will not prevent the user from subsequently manually inflating the cylinders. Namely, when pump bulb 18 is compressed, the force generated by the compression of the fluid through pump passageway 34 will be many times greater than any overpressure generated by the reservoir. To date, it has been very difficult to monitor and determine the pressures generated in an overpressure situation since each user exhibits unique individual characteristics. Furthermore, each spontaneous inflation may result from a very different physical act on the part of the user. Pressure generated by compression of the reservoir is believed to result in a fluid pressure of up to about 3 pounds per square inch but may be as high as 6–8 pounds per square inch. Conversely, compression of the pump bulb 18 will usually generate pressures on the order of 20 pounds per square inch. Clearly, the pressure generated by compression of the pump bulb 18 is sufficient to overcome the force generated by abutting wall 42, and allow fluid to move into the cylinders via fluid output 14. During a subsequent decompression of pump bulb 18, reservoir poppet 20 will be pulled away from its valve seat 24 and fluid will be drawn from bypass passageway 38 and fluid input 10 into pump chamber 36. Thus allowing the termination chamber 40 to return to its original state.

Figure 4:
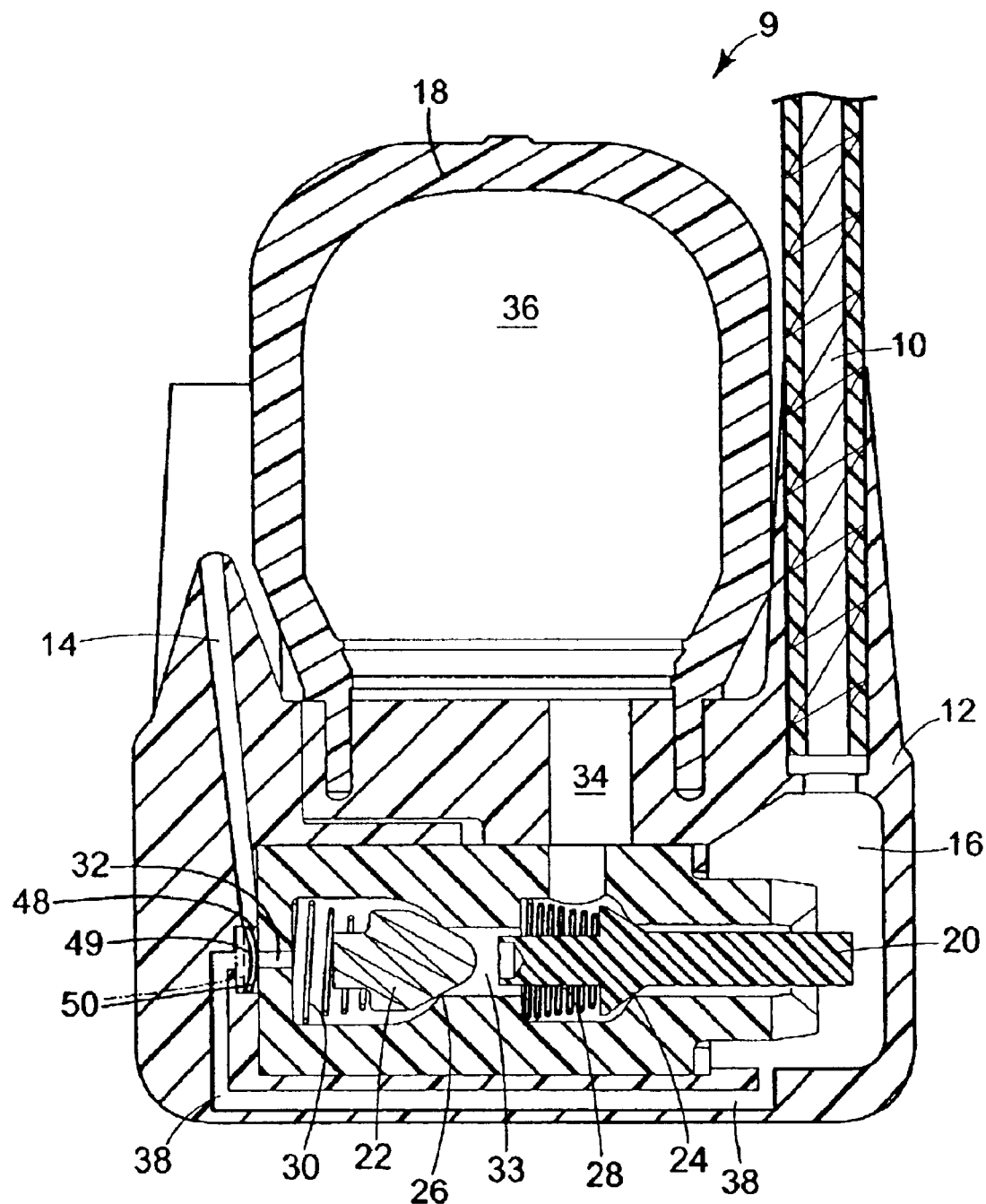
FIG. 4 is a side-sectional view of a penile pump having a diaphragm member between a bypass passageway and the cylinder poppet output.

Referring to FIG. 4, a second embodiment of the present invention is illustrated. Once again a bypass passageway 38 is provided. Bypass passageway 38 is fluidly coupled at one end to the input chamber 16. An expansion chamber 49 and a junction chamber 48 are provided at the opposite end of bypass passageway 38. Cylinder poppet output 32 (which is coupled with common passageway 33) is fluidly coupled to junction chamber 48. Finally, fluid output 14 is also fluidly coupled to junction chamber 48. Disposed between junction chamber 48 and expansion chamber 49 is a flexible diaphragm 50. During normal operation, flexible diaphragm is in the state represented by dashed lines. That is, flexible diaphragm 50 is flush against bypass passageway 38. When manually actuated, the pressurized fluid from the pump bulb 18 is forced through common passageway 33, bypassing cylinder poppet 22 and exiting through cylinder poppet output 32 into fluid output 14, unhindered by flexible diaphragm 50.

During an overpressure situation, the compressed fluid is forced from the reservoir through fluid input 10 and into input chamber 16. From input chamber 16, the pressurized fluid travels through bypass passageway 38 and into expansion chamber 49. The pressure generated will cause the flexible diaphragm 50 to flex to the position represented by solid lines. In this position, cylinder poppet output 32 is sealed. Thus, even if the overpressure is sufficient to dislodge the reservoir poppet 20 and the cylinder poppet 22 from their respective valve seats, fluid is prevented from entering fluid output 14 and spontaneously inflating the cylinders.

Once again, the overpressure of the fluid is used against itself to prevent fluid from entering the fluid output 14. As is illustrated, expansion chamber 49 is relatively large compared to cylinder poppet output 32. More specifically, once the flexible diaphragm 50 is in the position represented by solid lines, a larger surface area of the flexible diaphragm 50 will then be exposed to the expansion chamber 49 than is exposed to the cylinder poppet output 32. As such, with equal fluid pressure being generated in the bypass passageway 38, and the cylinder poppet output 32, a greater force will be exerted in the direction forcing flexible diaphragm 50 against cylinder poppet outlet 32, due to the relative surface area ratios. When the user wishes to manually inflate the cylinder, a compression of the pump bulb 18 will generate force in excess of that exerted on flexible diaphragm 50 through bypass passageway 38.

Figure 5:
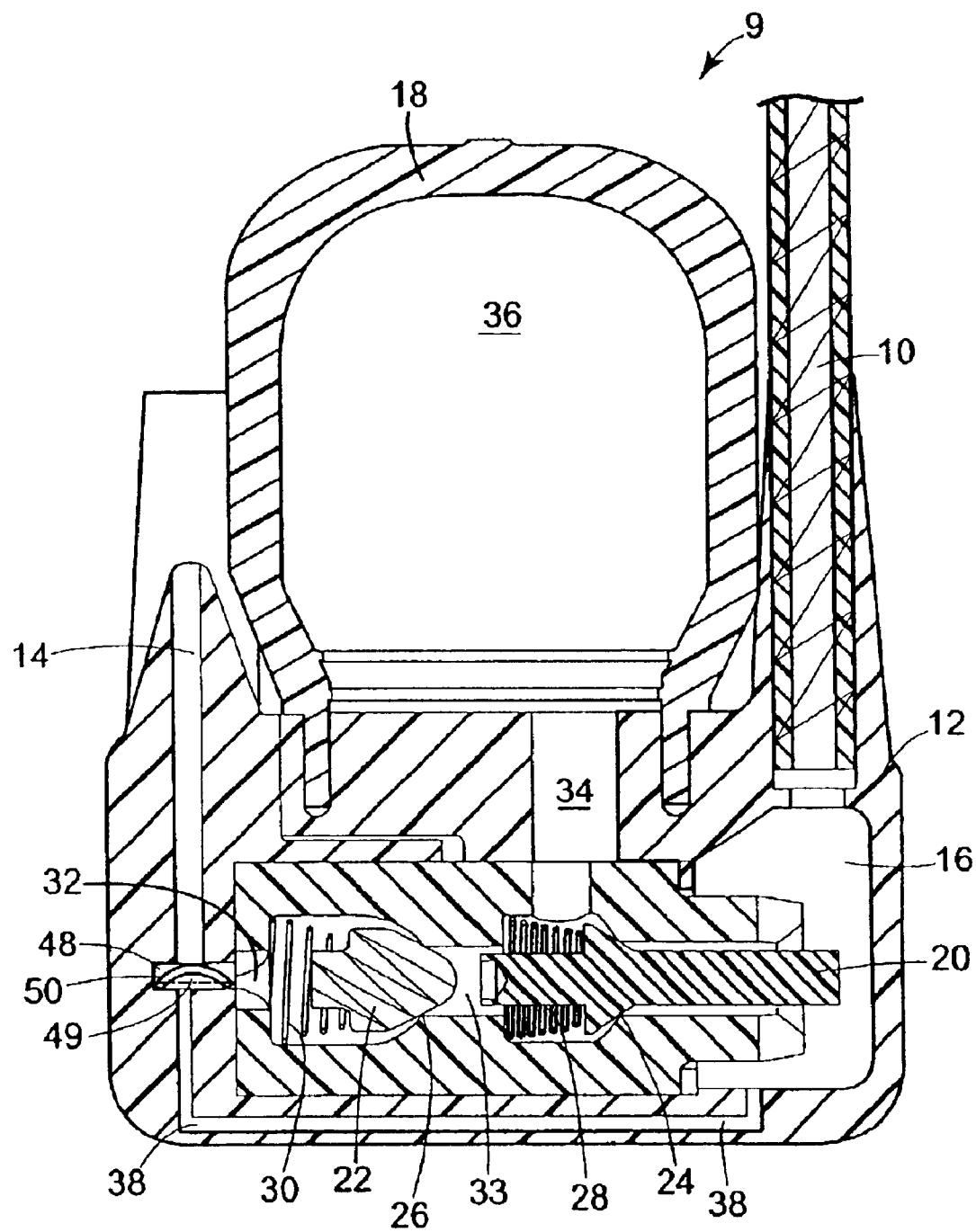
FIG. 5 is a side-sectional view of a penile pump having a diaphragm between the bypass passageway and the cylinder poppet output.

FIG. 5 illustrates a variation of the embodiment illustrated in FIG. 4. Here the flexible diaphragm 50 flexes between sealing the bypass passageway 38 and sealing the fluid output 14. Sealing the fluid output 14 effectively prevents fluid from exiting cylinder poppet output 32 and entering fluid output 14. Once again it is the amount of fluid surface area within expansion chamber 49 that is in contact with flexible diaphragm 50 versus the amount of fluid surface area in and around junction chamber 48 (also in contact with flexible diaphragm 50) that results in a sufficient force differential to seal fluid output 14.

In both the embodiments shown in FIGS. 4 and 5, it should be noted that if pressurized fluid were to exit out through cylinder poppet output 32 and thus exert a force against flexible diaphragm 50 before sufficient force was generated through bypass passageway 38, the sealing effects of flexible diaphragm 50 would effectively be bypassed and spontaneous inflation could occur. However, as is readily apparent from the illustrations, this will not happen. As overpressurization occurs in the reservoir, pressurized fluid is directed through fluid input 10 and into input chamber 16. The path of least resistance will be through bypass passageway 38 rather than displacing reservoir poppet 20 and cylinder poppet 22 from their respective valve seats. As such, flexible diaphragm 50 will always be flexed to its sealing position when an overpressure situation occurs, and this displacement will occur before either poppet 20 or 22 is displaced allowing fluid to flow through cylinder poppet output 32.

Figure 6:
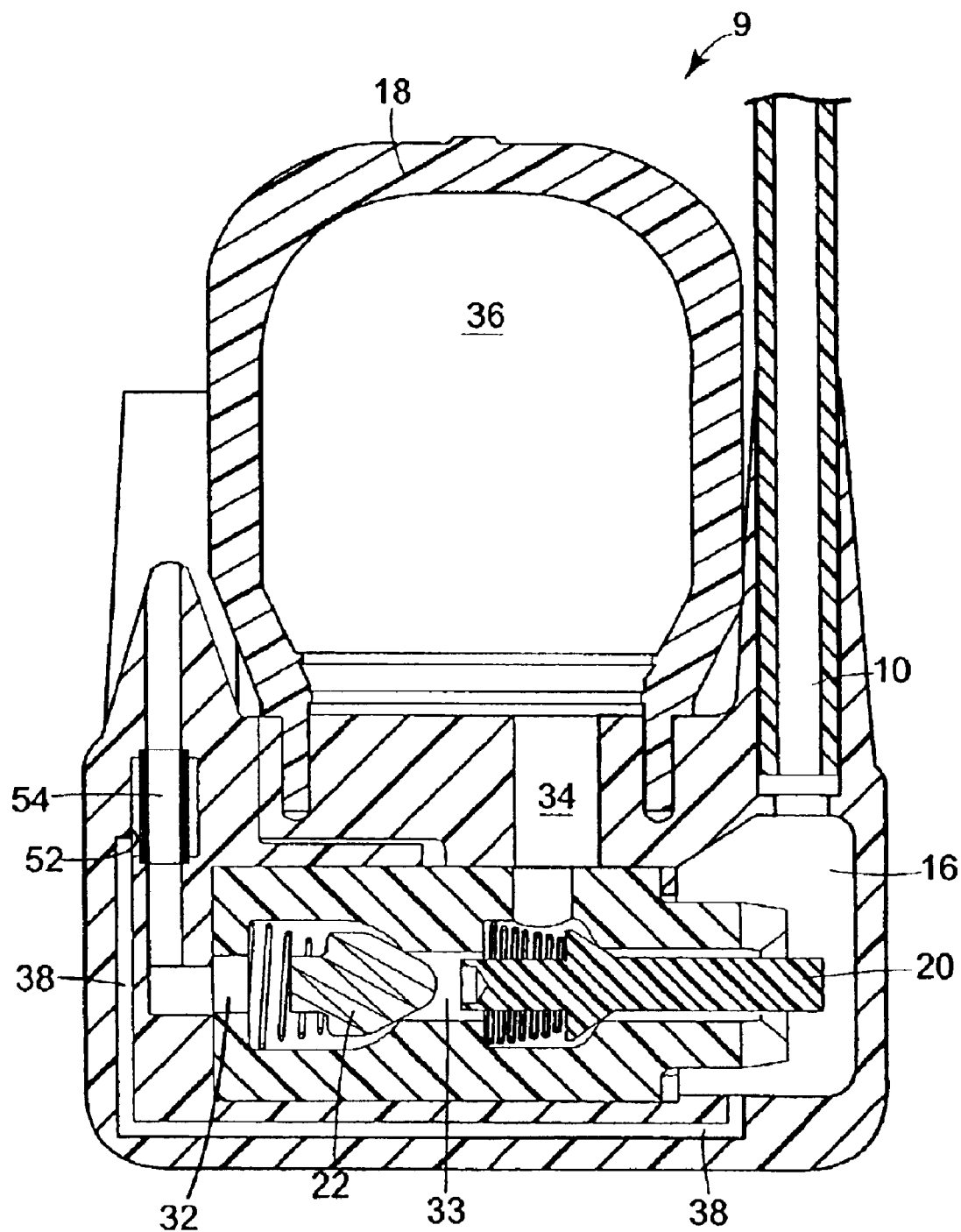
FIG. 6 is a side-sectional view of a penile pump having a bypass passageway which compresses a collapsible portion of the fluid output.

Referring to FIG. 6, a third embodiment of the present invention is illustrated. Bypass passageway 38 fluidly couples input chamber 16 to a compression chamber 52. Compression chamber 52 surrounds a portion of fluid output 14. If not already sufficiently flexible, the portion of the fluid output 14 within compression chamber 52 can be formed from a flexible, easily compressible material. During an overpressure situation, compressed fluid from the reservoir is forced through fluid input 10 and into input chamber 16. The compressed fluid flows through bypass passageway 38 and into compression chamber 52 where it compresses compressible tube 54 (which is that section of fluid output 14 within compression chamber 52). The amount of surface area on the outer surface of compressible tube 54 will necessarily be greater than the surface area within the compressible tube 54. As such, the force generated will be greater in a direction compressing compressible tube 54 than a counterforce trying to expand it. As such, when an overpressure situation occurs, compressible tube 54 is collapsed, sealing fluid output 14 from the cylinders and preventing spontaneous inflation.

Figure 7:
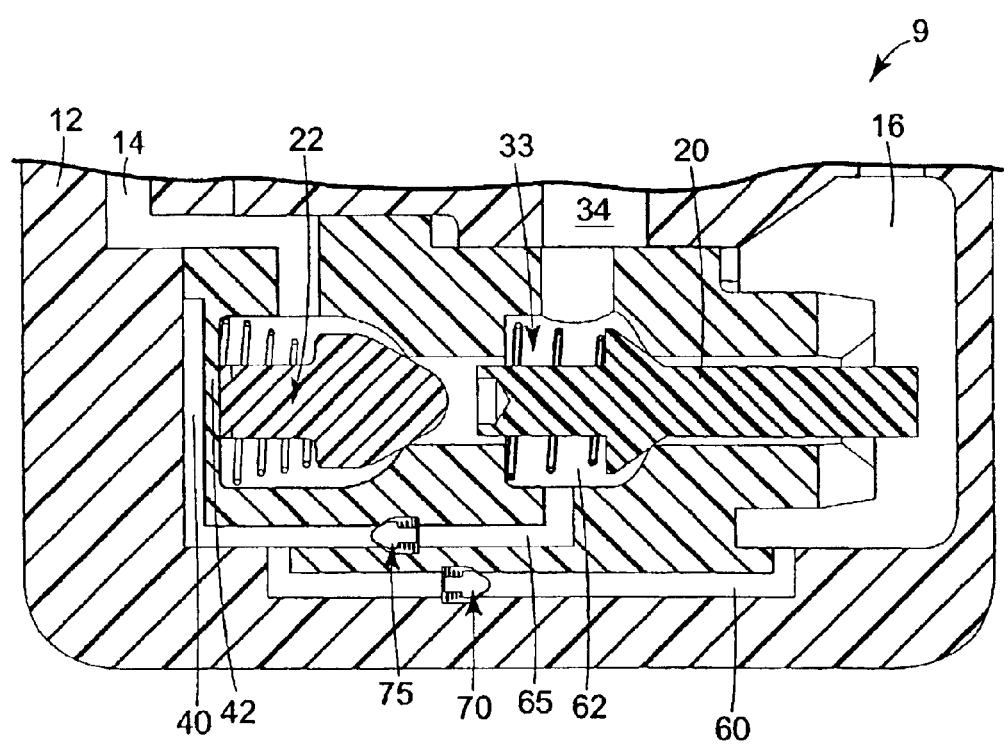
FIG. 7 is a side-sectional view of a penile pump having a bypass fluid passageway and a return fluid passageway with a check valve located in each.

FIG. 7 illustrates a fourth embodiment of the present invention. This embodiment has several elements that are in common with the previously described embodiments. Namely input chamber 16 is fluidly coupled to fluid output 14 via common passageway 33. Common passageway 33 is impeded by a reservoir poppet 20 and cylinder poppet 22 which are both spring biased to seat against their respective openings. The area between the nose of cylinder poppet 22 and the rear portion of reservoir poppet 20 is referred to as intermediate chamber 62.

The intermediate chamber 62 is fluidly coupled to a return channel 65 which is in fluid communication with expansion chamber 40. A return check valve 75 is provided within return channel 65 and only allows fluid flow from expansion chamber 40 to intermediate chamber 62. A bypass channel 60 is provided and fluidly couples input chamber 16 to return channel 65. As indicated the junction between the bypass channel 60 and return channel 65 occurs between expansion chamber 40 and return check valve 75. A bypass check valve 70 is provided within bypass channel 60 and only allows fluid flow in the direction from input chamber 16 to expansion chamber 40.

When an over-pressurization situation occurs, fluid pressure within input chamber 16 increases. This higher pressure fluid travels through bypass channel 60 and unseats bypass check valve 70. From here the pressurized fluid flows into the return channel 65 and into expansion chamber 40 or alternatively it unseats return check valve 75 and enters intermediate chamber 62. As fluid pressure is increased abutting wall 42 is caused to deflect due to the expansion of expansion chamber 40 and firmly abuts cylinder poppet 22 causing it to form a tight seal. Similarly fluid pressure levels within intermediate chamber 62 can increase, however, as previously discussed due to the differences in relative surface area the force exerted within expansion chamber 40 against abutting wall 42 will always be greater than that exerted against the nose of cylinder poppet 22, thus preventing spontaneous inflation.

As fluid pressures within input chamber 16 decrease the elevated fluid pressure level within intermediate chamber 62 cause reservoir poppet 20 to firmly seal and also cause return check valve 75 to firmly seal. (Assuming equal pressure within expansion chamber 40 and intermediate chamber 62). Bypass check valve 70 is also likewise sealed. Thus, the higher pressure fluid within expansion chamber 40 is effectively trapped and cannot exit unless the fluid pressure levels within intermediate chamber 62 are reduced which would allow return check valve 75 to open. In other words, fluid pressures within expansion chamber 40 will always be greater or equal to the fluid pressure levels within intermediate chamber 62.

With this embodiment fluid pressure levels within intermediate chamber 62 are only reduced when pump bulb 18 is actuated forcing cylinder poppet 22 to unseat itself and causing the cylinders to be inflated. Alternatively, housing 12 could be engaged in the manner described above to deflate the cylinders. That is manually actuating reservoir poppet 20 to disengage cylinder poppet 22. The release of reservoir poppet 20 would allow pressurized fluid within intermediate chamber 62 to reenter input chamber 16.

As fluid pressure levels within input chamber 16 increase the forces generated could either unseat reservoir poppet 20, thus allowing entry into intermediate chamber 62 or they could unseat bypass check valve 70, allowing fluid communication with expansion chamber 40. It is desirable to have fluid communication with expansion chamber 40 prior to fluid communication with intermediate chamber 62. Thus bypass check valve 70 is configured to open at lower pressures than reservoir poppet 20. As fluid pressures increase within input chamber 16 fluid will follow the path of least resistance, thus opening bypass check valve 70. Subsequently pressures may be sufficient to also open reservoir poppet 20, but the system will continue to work properly inasmuch as expansion chamber 40 is already expanding.

Figure 8:
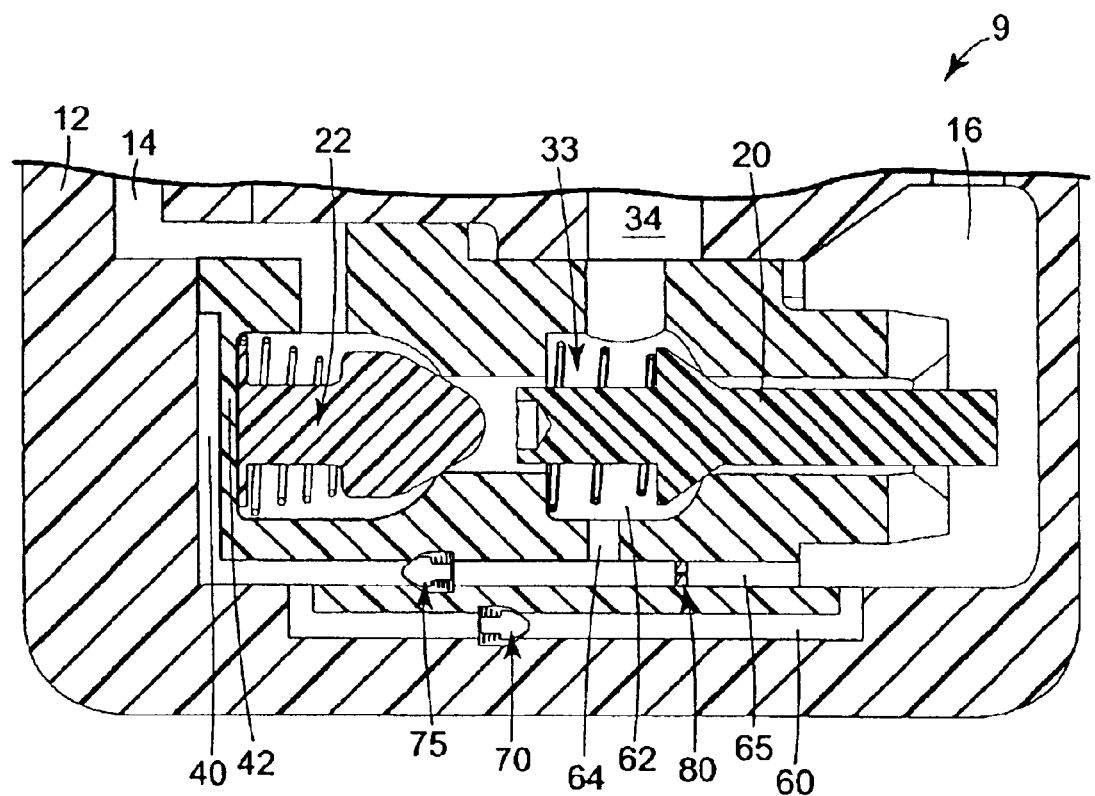
FIG. 8 is a side-sectional view of a penile pump having a bypass fluid passageway and a return fluid passageway with a check valve located in each and a fluid resistor located within the return fluid passageway.

A fifth embodiment of the present invention is illustrated in FIG. 8. A return channel 65 is provided which fluidly couples input chamber 16 to expansion chamber 40. Intermediate chamber 62 is fluidly coupled to return channel 65 via intermediate chamber passageway 64. Located within return channel 65 are a return check valve 75 and a fluid resistor 80. Return check valve 75 is positioned between intermediate chamber passageway 64 and expansion chamber 40 while fluid resistor 80 is positioned between intermediate chamber passageway 64 and input chamber 16. Bypass channel 60 is provided and fluidly couples input chamber 16 with return channel 65 wherein the junction between bypass channel 60 and return channel 65 occurs between the return check valve 75 and expansion chamber 40. Located within bypass channel 60 is a bypass check valve 70 that only allows fluid flow in the direction from input chamber 16 to expansion chamber 40. Return check valve 75 allows fluid flow from the direction of expansion chamber 40 towards both intermediate chamber 62 and input chamber 16.

As fluid pressures within input chamber 16 increase bypass check valve 70 is caused to be unseated allowing fluid flow into expansion chamber 40 as previously described. The cracking pressure required to unseat bypass check valve 70 is lower than that required to unseat reservoir poppet 20. Thus, pressurized fluid is caused to flow from input chamber 16 through bypass channel 60 and into expansion chamber 40, and if sufficient pressures are reached return check valve 75 can be unseated and pressurized fluid can enter intermediate chamber 62. Once again as pressure levels within expansion chamber 40 increase, abutting wall 42 is caused to deflect which in turn causes cylinder poppet 22 to firmly seal preventing spontaneous inflation.

As illustrated, input chamber 16 is in fluid communication with return channel 65. However, fluid resistor 80 is positioned between input chamber 16 and intermediate chamber 62. Fluid resistor 80 is a narrowing of a fluid passageway restricting fluid flow, a lengthening of the fluid path, or a combination of the two. Fluid resistor 80 could be a separate component added to the structure, rather than a modification of the existing passageway. Thus, during an over-pressurization situation fluid flow from input chamber 16 into intermediate chamber 62 through fluid resistor 80 is trivial. Conversely, during a compression of pump bulb 18, fluid resistor 80 will allow a small amount of bleed through into input chamber 16. This has a very negligible effect on pumping. As described with reference to the fourth embodiment, pressure levels within expansion chamber 40 and intermediate chamber 62 can each reach relatively high levels. Return check valve 75 will only allow pressurized fluid within expansion chamber 40 to exit when pressure levels within intermediate chamber 62 and the corresponding portion of return channel 65 are lower than that within expansion chamber 40. To allow this to occur fluid resistor 80 slowly allows pressurized fluid within intermediate chamber 62 to bleed back into input chamber 16. Over time pressure levels within intermediate chamber 62 and input chamber 16 will reach stasis. As pressure levels within intermediate chamber 62 are reduced, higher pressure fluid from expansion chamber 40 will unseat return check valve 75 and also eventually pass through fluid resistor 80 back into input chamber 16 returning the entire system to equilibrium.

Figure 9:
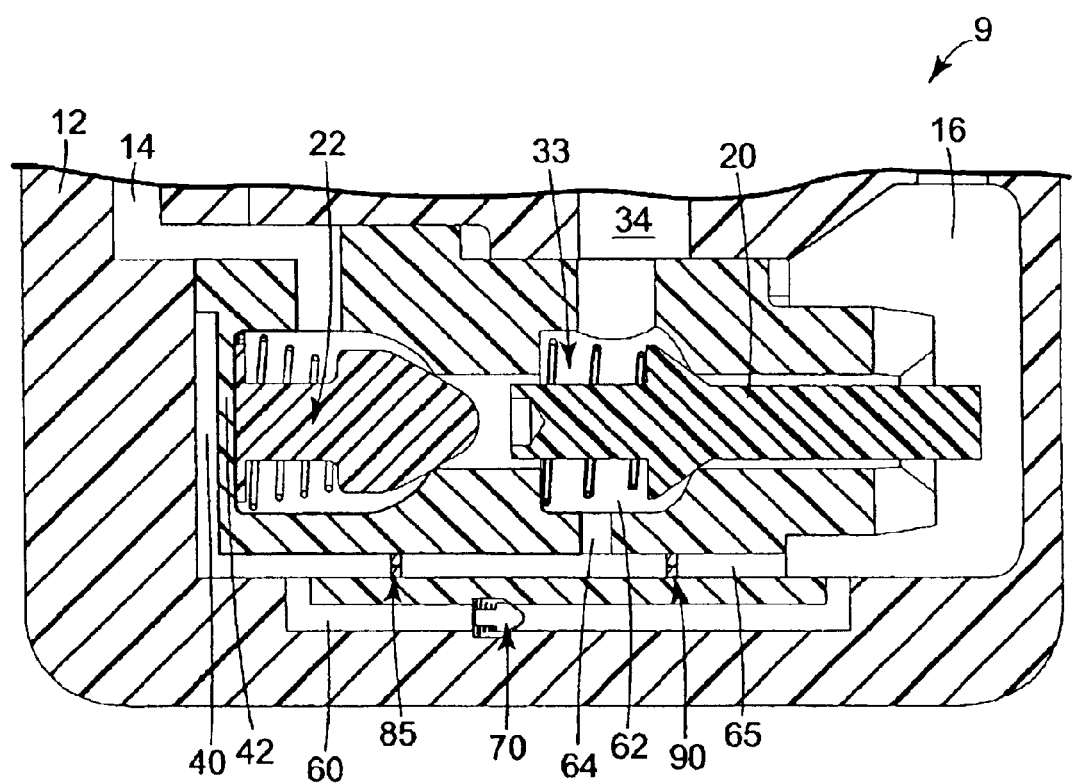
FIG. 9 is a side sectional view of a penile pump having a bypass fluid passageway and a return fluid passageway with a check valve located in the bypass fluid passageway and a pair of fluid resistors located within the return fluid passageway.

A sixth embodiment is shown with reference to FIG. 9. A return channel 65 is provided and fluidly couples input chamber 16 to expansion chamber 40. Intermediate chamber 62 is also fluidly coupled to return channel 65 via intermediate chamber passageway 64. Located between input chamber 16 and intermediate chamber passageway 64 is a reservoir side fluid resistor 90. Located between intermediate chamber passageway 64 and expansion chamber 40 is a cylinder side fluid resistor 85. Bypass channel 60 is provided and fluidly couples input chamber 16 to expansion chamber 40, effectively bypassing both fluid resistors 85 and 90. Bypass check valve 70 is provided within bypass channel 60 and allows fluid flow in the direction from input chamber 16 to expansion chamber 40.

As an over-pressurization situation occurs, pressurized fluid from input chamber 16 flows through bypass channel 60 and unseats bypass check valve 70 allowing fluid entry into expansion chamber 40. Pressurized fluid causes abutting wall 42 to deflect, thus sealing cylinder poppet 22 and preventing spontaneous inflation. Bypass check valve 70 has a lower cracking pressure than reservoir poppet 20 encouraging fluid flow through bypass channel 60 and into expansion chamber 40 prior to unseating reservoir poppet 20 and allowing pressurized fluid to flow into intermediate chamber 62. While return channel 65 is in fluid communication with both intermediate chamber 62 and expansion chamber 40, initially pressurized fluid from reservoir 16 will not quickly enter either of these two areas through return channel 65 due to restricted fluid flow through cylinder side fluid resistor 85 and reservoir side fluid resistor 90.

Once fluid pressure levels within input chamber 16 are reduced, high pressure fluids within intermediate chamber 62 will slowly bleed through reservoir side resistor 90 and into input chamber 16. As this occurs fluid pressure levels within return channel 65 will slowly decrease. When fluid pressure levels within return channel 65 on the input chamber side of cylinder side fluid resistor 85 are lower than that within expansion chamber 40, pressurized fluid will slowly bleed through cylinder side resistor 85 and eventually return to input chamber 16. Once again this system always maintains a higher pressure level within expansion chamber 40 than is maintained in intermediate chamber 62. Just as with the previous embodiment, there will be a small amount of pressure bleed through reservoir side resistor 90 into input chamber 16. This will have a negligible effect on pumping.

Figure 10:
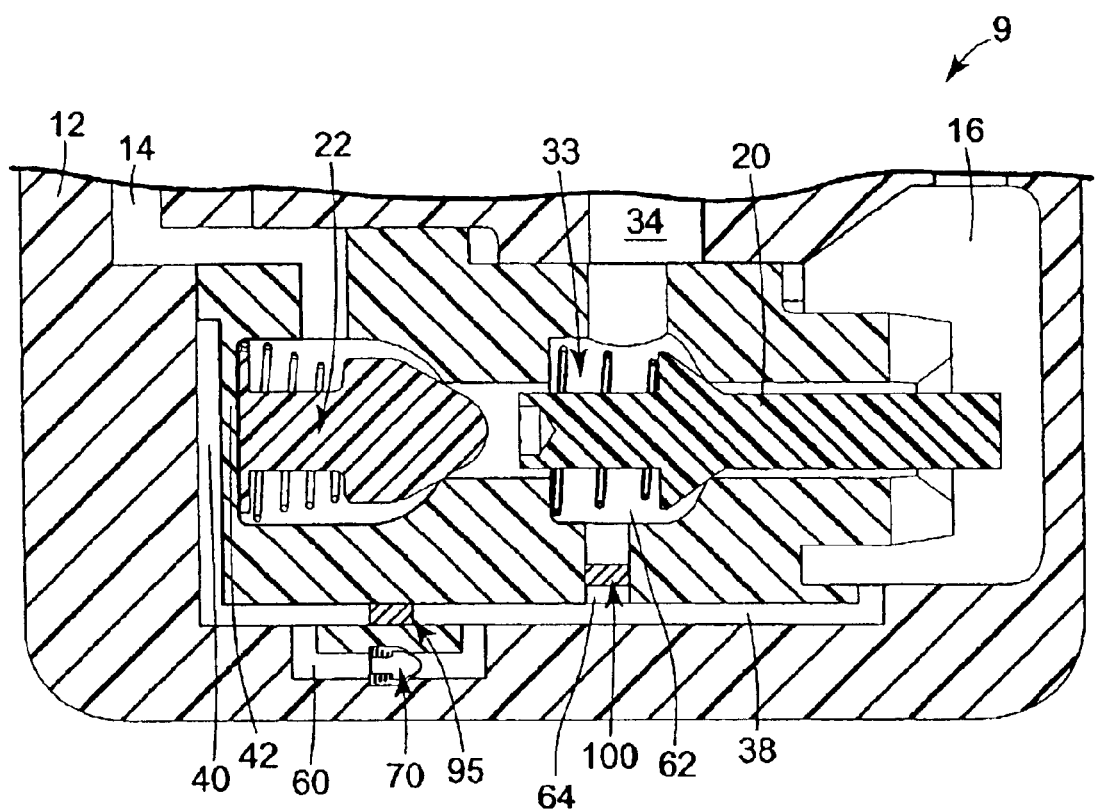
FIG. 10 is a side sectional view of a penile pump having a bypass fluid passageway with a pair of fluid resistors and a bypass channel with a check valve.

Referring to FIG. 10, a seventh embodiment to the present invention is illustrated. A bypass fluid passageway 38 fluidly couples input chamber 16 to expansion chamber 40. Located within bypass passageway 38 is a high impedance fluid resistor 95 Intermediate chamber passageway 64 fluidly couples intermediate chamber 62 to bypass passageway 38. Located within intermediate chamber passageway 64 is a low impedance fluid resistor 100 It is to be understood that with reference to fluid resistors 95 and 100 the terms high and low are with respect to one another. That is fluid resistor 100 has a lower fluid impedance than fluid resistor 95. In other words, a higher volume of fluid will travel through low impedance resistor 100 than through high impedance resistor 95 in the same amount of time when under the same pressure. Bypass channel 60 is provided and is coupled to bypass passageway 38, effectively bypassing the high impedance fluid resistor 95. Bypass check valve 70 is located within bypass channel 60 and only allows fluid flow in the direction from the input chamber 16 to expansion chamber 40. The cracking pressure of bypass check valve 70 is set such that when an over-pressurization situation occurs the path of least resistance from input chamber 16 is to enter bypass passageway 38, open bypass check valve 70, and enter expansion chamber 40. Pressurized fluid may eventually be able to unseat reservoir poppet 20 or flow through low impedance resistor 100 and enter intermediate chamber 62. However, the abutting wall 42 is displaced by the movement of expansion chamber 40 under increased fluid pressures causing cylinder poppet 22 to seal tightly preventing spontaneous inflation.

When fluid pressures are reduced in input chamber 16 high pressure fluid contained within intermediate chamber 62 passes more quickly through low impedance resistor 100 than would pass through high impedance resistor 95. Hence, intermediate chamber 62 empties at a faster rate. In addition, fluid will only travel from expansion chamber 40 through high impedance resistor 95 when fluid pressure levels within bypass passageway 38 adjacent input chamber 16 are sufficiently low. That is, lower than that within expansion chamber 40. This fact coupled with the ability of the intermediate chamber 62 to reduce pressure levels more quickly will always assure that pressure levels within expansion chamber 40 are higher than that within intermediate chamber 62 once again preventing spontaneous inflation. During pumping, a small amount of pressurized fluid will pass through low impedance resistor 100, however the effect will be negligible.

Figure 11:
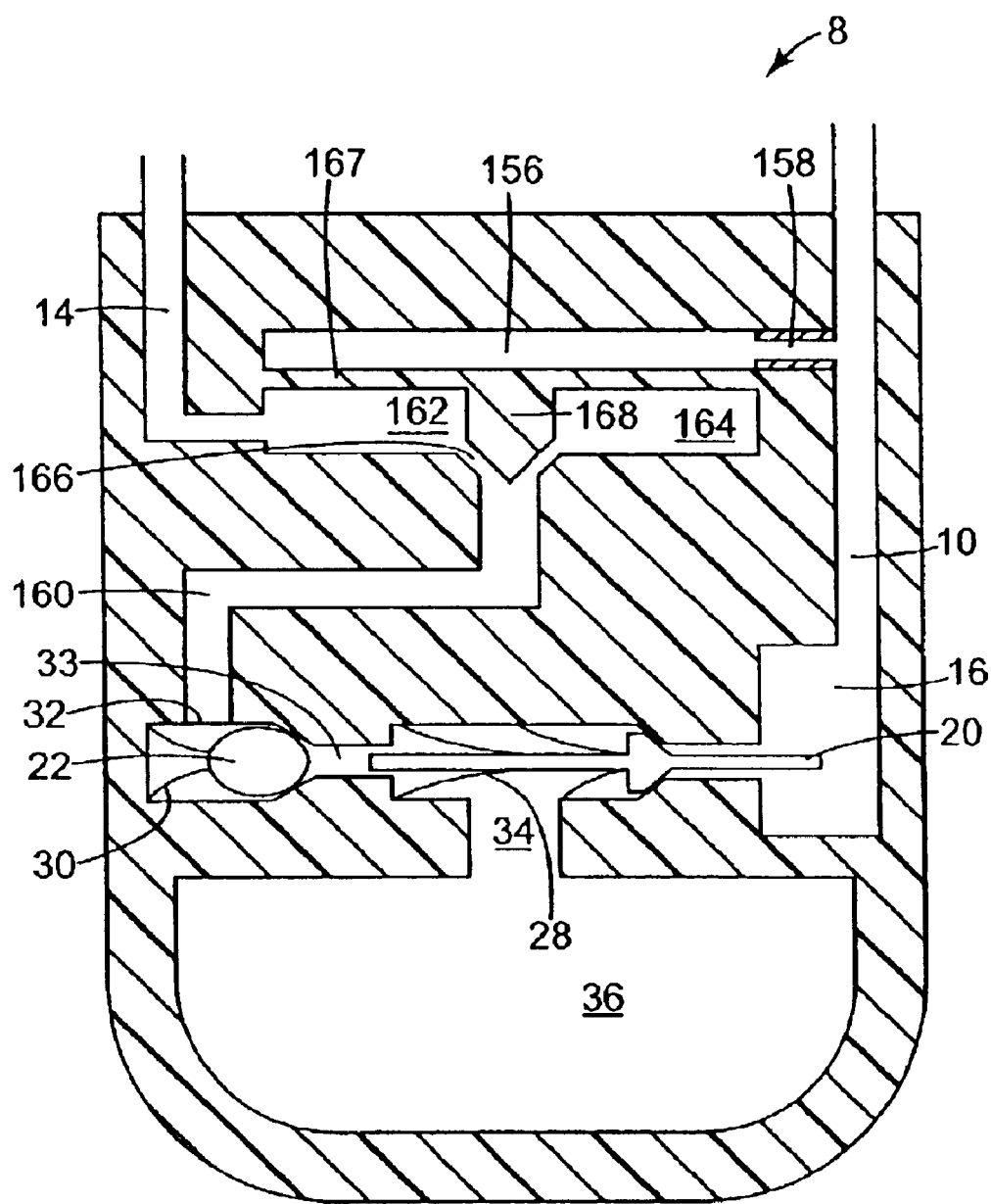
FIG. 11 is a side-sectional view of a penile pump having a fluid output that has a reduced throat portion that is sealable during an overpressurization situation.

FIG. 11 represents an eighth embodiment of the present invention. As illustrated, housing 12 has been slightly modified to accommodate a variety of additional internal passageways. Fluid input 10 is coupled with a reservoir at one end and reservoir chamber 16 at the other. Located within housing 12, and coupled to fluid input 10 prior to reservoir chamber 16, is an overpressure chamber 156. Optionally, overpressure chamber 156 has an overpressure chamber input 158 having a narrowed opening. Cylinder poppet output 32 leads into an output passageway 160. Output passageway 160 leads to a first output chamber 162 and a second output chamber 164 (actually two parts of a single chamber or passage way). The fluid output 14 is fluidly coupled to the first output chamber 162. Interconnecting the output passageway 160 to the first output chamber 162 is a relatively narrow throat portion 166. The first output chamber 162 and the second output chamber 164 are located proximate the overpressure chamber 156 within housing 12. Separating first output chamber 162 and second output chamber 164 is a compression wall 167 with a sealing extension 168 which also forms a portion of the narrow throat portion 166. During an overpressure situation, fluid pressure is increased in overpressure chamber 156, thus causing it to expand. The expansion of overpressure chamber 156 causes the compression wall 167 and sealing extension 168 to move, thus sealingly abutting throat 166 and effectively preventing fluid from flowing through output passageway 160. Preferably, compression wall 167 is configured so that a maximum amount of movement results from the force generated, thus effectively sealing throat 166.

Figure 12:
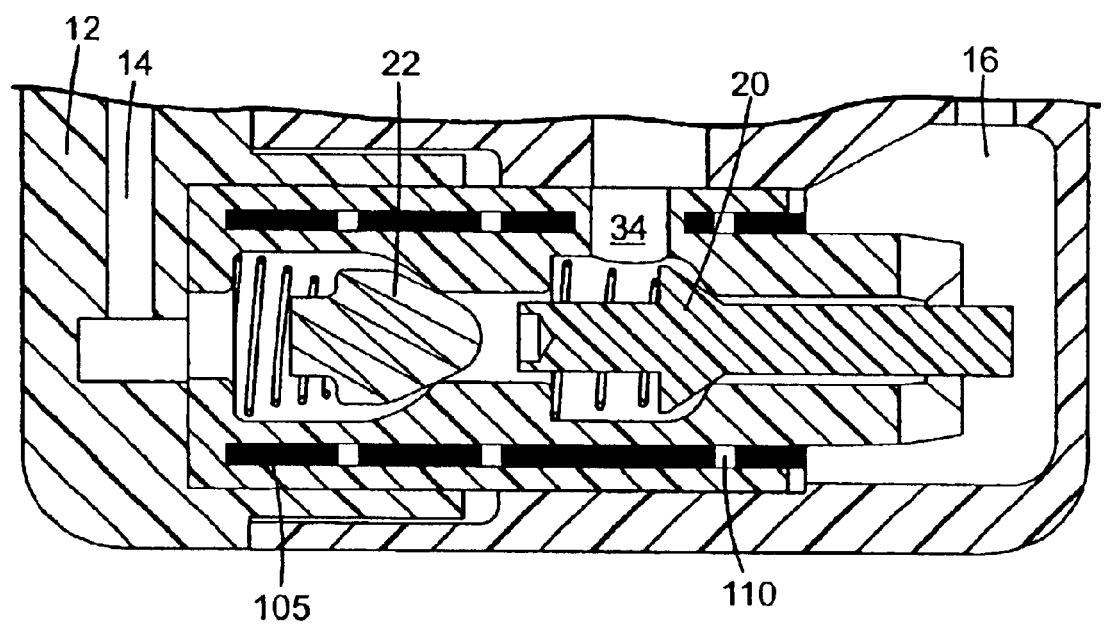
FIG. 12 is a side sectional view of a penile pump having a rigidifying cylindrical element located within the housing.

Referring to FIG. 12 a ninth embodiment to the present invention is illustrated. This embodiment can be used as shown or can be coupled with any of the previously described embodiments. Generally the housing 12 of the valve assembly will be made of a flexible material such as silicone. As such if external pressures are applied to housing 12 in an undesired manner, it may be possible to unseat poppets 20, 22 which may lead to spontaneous inflation. To prevent an inadvertent compression of housing 12 from causing spontaneous inflation, a rigid insert is incorporated into housing 12 to eliminate this degree of flexibility.

As shown in FIG. 12 a solid cylindrical element 105 is incorporated within housing 12 and surrounds reservoir poppet 20 and cylinder poppet 22. Thus, inadvertent compression of housing 12 will be unable to displace reservoir poppet 20 or cylinder poppet 22. Of course, to function properly the user must be able to manually displace reservoir poppet 20 by compressing the side walls of housing 12 and this function is maintained.

Since the housing 12 for the valve assembly is generally molded, it may be desirable to have cylindrical element 105 in place during the fabrication process by including a plurality of holes 110 in cylindrical element 105 and placing cylindrical element 105 in the mold during fabrication. Cylindrical element 105 will in effect be molded in place and holes 110 allow the material being utilized (i.e. silicone) to flow through cylindrical element 105 and properly define housing 12. While shown as being cylindrical, element 105 can be formed into any appropriate shape for the valve assembly being utilized.

In general the present invention utilizes an outlet sealing mechanism that relies on the overpressure generated by a compression of the reservoir (or similar component) to also seal the output. That is, the overpressure generated is effectively used against itself to prevent fluid from entering the cylinder and producing a spontaneous inflation. While various embodiments have been shown and described which utilize this effect, it is to be understood that any such utilization of the overpressure to prevent fluid flow to the cylinders is within the scope and spirit of the present invention, and as such, the present invention is not intended to be limited only to those specific embodiments shown and described herein.

While the present invention has been described with respect to a pump and valve assembly for a penile implant, the use of generated overpressure to seal a fluid aperture has many other applications within the scope and spirit of the present invention. For example, artificial sphincters utilize fluid pressure to maintain a body cavity or natural passageway in a closed or sealed state. When actuated, fluid pressure is released from the sphincter, causing the bodies' passageway to open. As such, the fluid pressure generated could be used to assist the artificial sphincter in either state. Likewise, many other uses for an overpressure seal exist, both specifically within the field of medical devices and within the field of fluid/gas handling devices in general.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. An inflation inhibitor for an implantable prosthesis, comprising:
    a housing in communication with an attached pump bulb; the housing having a fluid passageway, the fluid passageway having an inlet and an outlet;
    a first flow valve controlling the inlet of the fluid passageway and located within the fluid passageway between the inlet and the outlet; and
    an outlet sealing mechanism located within the housing that selectively and substantially seals the flow of fluid from the inlet to the outlet in response to a fluid pressure increase within at least a portion of the housing adjacent to the inlet of the fluid passageway that exceeds a predetermined level.

2. The inflation inhibitor of claim 1 wherein fluid pressure controls the outlet sealing mechanism.

3. The inflation inhibitor of claim 1, further comprising a second flow valve located within the fluid passageway.

4. The pump assembly of claim 1 wherein the outlet sealing mechanism further comprises:
    an overpressure chamber fluidly coupled to the inlet; and
    an output passageway forming a part of the fluid passageway between the first flow valve and the outlet, wherein the output passageway includes a narrow throat portion located proximate the overpressure chamber so that when the fluid pressure within the overpressure chamber exceeds a predetermined value an expansion of the overpressure chamber occurs which causes the throat portion to close.

5. The pump assembly of claim 4, further comprising:
    a first output chamber, forming part of the output passageway; and
    a second output chamber, forming part of the output passageway, so that the first and second output chambers form a moveable compression wall that is coupled with the overpressure chamber so that expansion of the overpressure chamber causes the compression wall to move which closes the throat portion.

6. An inflation inhibitor for an implantable prosthesis, comprising:
    a housing having a fluid passageway, the fluid passageway having an inlet and an outlet;
    a first flow valve located within the fluid passageway between the inlet and the outlet; and
    an outlet sealing mechanism located within the housing that selectively and substantially seals the flow of fluid from the inlet to the outlet in response to a fluid pressure increase within at least a portion of the housing that exceeds a predetermined level, wherein the outlet sealing mechanism includes a bypass passageway having a first end which is in fluid communication with the inlet and a second end which is in fluid communication with a chamber, wherein the amount of fluid pressure within the chamber selectively prevents fluid flow through the outlet.

7. The inflation inhibitor of claim 6, further comprising:
    a flexible abutting wall disposed between the chamber and the first flow valve so that the abutting wall is caused to contact the first flow valve and urge the first flow valve into a closed position when the fluid pressure within the chamber exceeds a predetermined amount.

8. The inflation inhibitor of claim 7 wherein a planar surface area of the abutting wall that is disposed within the chamber is larger than a surface area of a portion of the first flow valve located within an inlet side of the fluid passageway when the first flow valve is in the closed position.

9. The inflation inhibitor of claim 8, further comprising a second flow valve disposed within the fluid passageway, between the inlet and the first flow valve.

10. The pump assembly of claim 6, further comprising:
    a diaphragm located within the chamber, the chamber being in fluid communication with the fluid passageway and the outlet so that when the diaphragm is in a first position, fluid is able to flow from the fluid passageway and through the outlet, and when the diaphragm is in a second position, no fluid is allowed to flow through the outlet.

11. The pump assembly of claim 10 wherein the diaphragm is caused to move to the second position when fluid pressure within the chamber exceeds a predetermined level.

12. The pump assembly of claim 10 wherein an amount of surface area on the diaphragm that is exposed to the bypass passageway is larger than an amount of surface area on the diaphragm that is exposed to the fluid passageway.

13. The pump assembly of claim 6 wherein the chamber surrounds a collapsible portion of the outlet and when the fluid pressure within the chamber exceeds a predetermined level the collapsible portion of the outlet is caused to collapse which prevents fluid flow through the outlet.

14. A pressure lock out arrangement for an inflatable prosthesis comprising:
a housing having an inlet and an outlet;
a valve disposed between the inlet and the outlet;
the valve being biased toward substantially sealing the outlet; and
a supplemental biasing mechanism responsive to pressure increases from the inlet to increase the biasing of the valve toward substantially sealing the outlet, wherein the supplemental biasing mechanism includes a bypass passageway having a first end which is in fluid communication with the inlet and a second end which is in fluid communication with a chamber, wherein the amount of fluid pressure within the chamber selectively prevents fluid flow through the outlet.

15. The pressure lock out of claim 14, further comprising:
a flexible abutting wall disposed between the chamber and the valve so that the abutting wall is caused to contact the valve and urge the valve into a closed position when the fluid pressure within the chamber exceeds a predetermined amount.

16. The pressure lock out of claim 14 further comprising:
a diaphragm located within the chamber, the chamber being in fluid communication with the inlet and the outlet so that when the diaphragm is in a first position, fluid is able to flow from the inlet and through the outlet, and when the diaphragm is in a second position, no fluid is allowed to flow through the outlet.

17. The pressure lock out of claim 14 wherein the chamber surrounds a collapsible portion of the outlet and when the fluid pressure within the chamber exceeds a predetermined level the collapsible portion of the outlet is caused to collapse which prevents fluid flow through the outlet.

18. An inflation inhibitor for an inflatable prosthesis comprising:
a housing having an inlet and an outlet;
a valve controlling fluid flow between the inlet and the outlet; and
an outlet sealing mechanism responsive to pressure increases from the inlet;
the valve and the outlet sealing mechanism being integrated and substantially enclosed in the housing, wherein the outlet sealing mechanism includes a bypass passageway having a first end which is in fluid communication with the inlet and a second end which is in fluid communication with a chamber, wherein the amount of fluid pressure within the chamber selectively prevents fluid flow through the outlet.

19. The inflation inhibitor of claim 18 further comprising:
a flexible abutting wall disposed between the chamber and the valve so that the abutting wall is caused to contact the valve and urge the valve into a closed position when the fluid pressure within the chamber exceeds a predetermined amount.

20. The pump and valve assembly of claim 18, further comprising:
a diaphragm located within the chamber, the chamber being in fluid communication with the inlet and the outlet so that when the diaphragm is in a first position, fluid is able to flow from the inlet and through the outlet, and when the diaphragm is in a second position, no fluid is allowed to flow through the outlet.

21. The pump and valve assembly of claim 18 wherein the chamber surrounds a collapsible portion of the outlet and when the fluid pressure within the chamber exceeds a predetermined level the collapsible portion of the outlet is caused to collapse which prevents fluid flow through the outlet.

22. An inflation inhibitor for an implantable prosthesis, comprising:
a housing having a fluid passage way, the fluid passageway having an inlet and an outlet, wherein the inlet is in fluid communication with a reservoir;
a first flow valve located within the fluid passageway between the inlet and the outlet;
a second flow valve located within the fluid passageway between the first flow valve and the inlet, wherein an intermediate chamber is defined between the first flow valve and the second flow valve within the fluid passageway;
an expansion chamber in fluid communication with the inlet; and
a flexible member located within the expansion chamber that selectively and substantially seals the outlet in response to a fluid pressure increase within the expansion chamber that exceeds a predetermined level, wherein the flexible member is an abutting wall disposed between the expansion chamber and the first flow valve so that the abutting wall is caused to contact the first flow valve and urge the first flow valve into a closed position when the fluid pressure within the chamber exceeds a predetermined amount.

23. An inflation inhibitor for an implantable prosthesis, comprising:
a housing having a fluid passageway, the fluid passageway having an inlet and an outlet, wherein the inlet is in fluid communication with a reservoir;
a first flow valve located within the fluid passageway between the inlet and the outlet;
a second flow valve located within the fluid passageway between the first flow valve and the inlet, wherein an intermediate chamber is defined between the first flow valve and the second flow valve within the fluid passageway;
an expansion chamber within the housing in fluid communication with the inlet; and
a flexible member located within the expansion chamber that selectively and substantially seals the outlet in response to a fluid pressure increase within the expansion chamber that exceeds a predetermined level.

24. The pump assembly of claim 23 wherein the flexible member is a diaphragm that selectively seals the outlet.

25. The pump assembly of claim 23, further comprising:
a return channel coupling the intermediate chamber and the expansion chamber;
a first check valve located within the return channel and only permitting fluid flow in the direction from the expansion chamber to the intermediate chamber;
a bypass channel coupling the inlet and the expansion chamber; and
a second check valve located within the bypass channel and only permitting fluid flow in the direction from the inlet to the expansion chamber.

26. The pump assembly of claim 25 wherein the second check valve has a first cracking pressure that is lower than a second cracking pressure of the second flow valve.

27. The pump assembly of claim 23, further comprising:
a return channel fluidly coupling the inlet, the intermediate chamber and the expansion chamber;
a fluid resistor located within the return channel between the inlet and the intermediate chamber;
a first check valve located within the return channel between the intermediate chamber and the expansion chamber that only allows fluid flow in a direction from the expansion chamber towards the intermediate chamber;
a bypass channel fluidly coupling the inlet to the expansion chamber; and
a second check valve located within the bypass channel that only allows fluid flow in a direction from the inlet towards the expansion chamber.

28. The pump assembly of claim 27 wherein the second check valve has a first cracking pressure that is lower than a second cracking pressure of the second flow valve.

29. The pump assembly of claim 23, further comprising:
a return channel fluidly coupling the inlet, the intermediate chamber and the expansion chamber;
a first fluid resistor located within the return channel between the inlet and the intermediate chamber;
a second fluid resistor located within the return channel between the intermediate chamber and the expansion chamber;
a bypass channel fluidly coupling the inlet to the expansion chamber; and
a first check valve located within the bypass channel that only allows fluid flow in a direction from the inlet towards the expansion chamber.

30. The pump assembly of claim 29 wherein the first check valve has a first cracking pressure that is lower than a second cracking pressure of the second flow valve.

31. The pump assembly of claim 23, further comprising:
a bypass passageway fluidly coupling the inlet to the expansion chamber;
an intermediate passageway fluidly coupling the intermediate chamber to the bypass passageway;
a first fluid resistor located within the intermediate passageway and impeding fluid flow between the intermediate chamber and the bypass passageway;
a second fluid resistor located within the bypass passageway;
a bypass channel fluidly coupling portions of the bypass passageway on opposite sides of the second fluid resistor, effectively bypassing the second fluid resistor within the bypass passageway; and
a first check valve located within the bypass channel that only allows fluid flow in a direction from the inlet towards the expansion chamber.

32. The pump assembly of claim 31 wherein the first fluid resistor passes a higher volume of fluid per unit time than the second fluid resistor.

33. The pump assembly of claim 31 wherein the second fluid resistor is located between the expansion chamber and the intermediate passageway.

* * * * *